United States Patent
Kishi et al.

(10) Patent No.: US 7,391,177 B2
(45) Date of Patent: Jun. 24, 2008

(54) MASTER-SLAVE MANIPULATOR SYSTEM AND THIS OPERATION INPUT DEVICES

(75) Inventors: Kosuke Kishi, Hitachinaka (JP); Kazuhiro Umekita, Tsuchiura (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/434,900

(22) Filed: May 17, 2006

(65) Prior Publication Data

US 2006/0261770 A1 Nov. 23, 2006

(30) Foreign Application Priority Data

May 20, 2005 (JP) ............................. 2005-147786

(51) Int. Cl.
*G05B 19/10* (2006.01)
(52) U.S. Cl. ............... 318/567; 318/568.12; 318/568.25
(58) Field of Classification Search ................. 318/567, 318/568.13, 568.2, 568.25
See application file for complete search history.

(56) References Cited

U.S. PATENT DOCUMENTS

| | | | |
|---|---|---|---|
| 5,399,951 A | | 3/1995 | Lavellee et al. |
| 5,672,044 A | * | 9/1997 | Lemelson ................. 414/744.3 |
| 5,792,135 A | * | 8/1998 | Madhani et al. ................. 606/1 |
| 6,233,504 B1 | | 5/2001 | Das et al. |
| 6,437,771 B1 | | 8/2002 | Rosenberg et al. |
| 2001/0020200 A1 | * | 9/2001 | Das et al. .................... 700/260 |
| 2004/0106916 A1 | * | 6/2004 | Quaid et al. .................... 606/1 |
| 2004/0199147 A1 | | 10/2004 | Nishizawa et al. |

FOREIGN PATENT DOCUMENTS

| | | |
|---|---|---|
| JP | 07-124876 | 5/1995 |
| JP | 11-333764 | 12/1999 |
| JP | 2004-223128 | 8/2004 |

OTHER PUBLICATIONS

Koyama et al, "Multi-Fingered Exoskeleton Haptic Device Using Passive Force Feecback For Dexterous Teleoperation", Proceedings of The 2002/IEEE/RSJ International Conference on Intelligent Robots and Systems, Lausanne, Switzerland, Sep. 30-Oct. 4, 2002, vol. 1 of 3, Sep. 2002 pp. 2905-2910.

* cited by examiner

*Primary Examiner*—Rina I. Duda
(74) *Attorney, Agent, or Firm*—Antonelli, Terry, Stout & Kraus, LLP.

(57) ABSTRACT

In a master-slave manipulator system capable of presenting an obstacle and a limit to an operating range as a force feedback with no use of a motor in an operation input device and having high reliability, a small size and good operability, the system comprises a manipulator having an arm, an operation input device for moving the arm of the manipulator, and a controller for controlling the manipulator and the operation input device, and the operation input device is provided on joints with a mode change-over mechanism having three modes: of which, in a first mode, power is not transmitted; in a second mode, power is transmitted in one direction and is not transmitted in a reverse direction thereof; and in a third mode, power is transmitted in the reverse direction and is not transmitted in the one direction, selecting one of the above modes and changing over from one mode to the selected mode.

10 Claims, 6 Drawing Sheets

MASTER-SLAVE MANIPULATOR SYSTEM AND THIS OPERATION INPUT DEVICES

BACKGROUND OF THE INVENTION

The present invention relates to a master-slave manipulator system and this operation input devices.

DESCRIPTION OF RELATED ART

There have been developed many master-slave manipulator systems in which a manipulator is operated by an operation input device manipulated by the operator.

However, in a usual master-slave manipulator system, even if an obstacle, a hazard area or the like to be avoided is present in an operation range of a manipulator arm, when the operation input device is moved to a position corresponding to the obstacle or the hazard area, the manipulator arm would hit the obstacle or enter the hazard area, which is caused a problem.

In order to solve the above-mentioned problem, JP-A-7-124876 (patent document 1) discloses such a configuration that a position restricting member is arranged in an operation range of an operation input device, corresponding to a position of an obstacle against the manipulator arm, in order to prevent the operation input device from entering an area where the operation of the manipulator arm is inhibited.

Further, JP-A-2004-223128 (patent document 2) discloses a configuration in which data of an operation range of a manipulator arm is previously acquired from a diagnostic tool, and an area where the manipulator arm can move for treatment is set according to the data, and when the operator comes near to move the manipulator arm out of the set area, a motor provided in an operation input device restricts the operation range of the operation input device so as to prevent the manipulator arm from moving out of the set area.

Further, in JP-A-11-333764 (patent document 3), when the arm makes contact with the object, a variable power transmission unit gives a force feedback to an operation input device, so as to make to feel a resistive force.

In the conventional master-slave manipulator systems, for preventing the operation input device from moving in an area where the operation of the manipulator arm is inhibited, an operation input device is provided with an actuator for feeding back a force to the operator, so as to restrict the operation of the operation input device. However, the actuator provided in the operation input device would cause an increase in the size of the operation input device, and additionally, a failure thereof or the like results in an excessive large force applied to the operator.

Should the operation range and a wall be exhibited as a force feed-back with the use of the actuator in the operation input device, the manipulator system causes problems of complicated control and vibrating behavior at an interface between a zone where a wall is sensed and a free operation zone.

Further, in a circumstance where noise causes a problem, a usual motor could be hardly used as the actuator. For example, a surgical support manipulator system utilizing an MRI unit as a diagnostic tool can hardly use an operation input device utilizing a motor which would cause noise interference with the MRI unit.

It is noted that, in the configuration disclosed in the patent document 1, there is not required a motor because of restricting the operation range of the operation input device by physically arranging the position restricting member and pins, but it is difficult to control the operation, in a case that the position of an obstacle or a possible operation range varies momentarily.

Further, the configuration disclosed in the patent document 2 discloses a method of setting a range where the manipulator arm can be operated, but, does not involve the use of any actuator other than the motor for restricting a possible operation range of the operation input device.

The patent document 3 discloses the proposal of presenting a force feed-back in the operation input device when the slave arm makes contact with an object, but it is not adapted to be use for avoiding an obstacle or a hazard zone. Further, it also discloses the mechanism that when the manipulator arm does not make contact with the object the operation is not influenced by a motor with the use of the variable power transmission unit. But even if the manipulator arm makes contact with the object, a force feed-back is presented with the use of a power from the motor.

BRIEF SUMMARY OF THE INVENTION

An object of the present invention is to provide a master-slave manipulator system and an operation input device therefor, which are capable of presenting an obstacle or a limit to an operation range as a force feed-back with no use of a motor in the operation input device, and which have high reliability, a small-size and good operability.

To the above-mentioned end, according to a first aspect of the present invention, there is provided a master-slave manipulator system comprising a manipulator having an arm, an operation input device for moving the arm of the manipulator, and a controller for controlling the manipulator and the operation input device, and the operation input devise comprises on joints a mode change-over mechanism. In this application, it is defined that the mode change-over mechanism has three modes: of which, in a first mode, power is not transmitted; in a second mode, power is transmitted in one direction and is not transmitted in a reverse direction thereof; and in a third mode, power is transmitted in the reverse direction and is not transmitted in the one direction, selects one of the above modes and changes over from one mode to the selected mode.

Specific configurations according to the first aspect of the present invention are as follows:

(1) A master-slave manipulator comprising a sensor or a diagnostic tool capable of acquiring geometrical data or obstacle data in an operation rage of the arm of the manipulator, and a means for setting an area where the arm of the manipulator can be operated, in accordance with the geometrical data or the obstacle data detected by the sensor or the diagnostic tool in the operation range of the arm of the manipulator, wherein the controller causes the mode change-over mechanism provided on each of the joints of the operation input devise, to restrain the operation input device from operating the arm of the manipulator in an area where the operation of the arm of the manipulator is inhibited, when the arm of the manipulator is to be operated by the operation input device in the area where the operation of the arm of the manipulator is inhibited.

(2) The mode change-over mechanism provided on each of the joints of the operation input device comprises a two-way clutch, a 3 position solenoid, and a translation joint mechanism using a rack and a pinion.

(3) The mode change-over mechanism provided in each of the joints of the operation input device comprises a two-way clutch, a 3 position solenoid and a rotating joint mechanism using two links constituting a joint.

(4) The operation input device comprises a grip opening and closing mechanism capable of having the functions of the mode change-over mechanism, and as well capable of optionally limiting the degree of opening of the grip.

(5) An MRI unit is used as the diagnostic tool for acquiring the geometrical data in the operation range of the arm of the manipulator.

(6) A CT unit is used as the diagnostic tool for acquiring the geometrical data in the operation range of the arm of the manipulator.

(7) The controller is constituted to control the selection of the mode change-over mechanism so as to limit the operation range of the arm of the manipulator.

(8) The controller is constituted to present a force feed-back when the arm of the manipulator makes contact with an object, by selecting the mode of the mode change-over mechanism multiple times and in a variable manner of duty ratio of disconnection and connection so as to finely change over the connection.

Further, according to a second aspect of the present invention, there is provided an operation input device for moving an arm of a manipulator in a master-slave manipulator system, comprising on joints thereof, a mode change-over mechanism which has three modes: of which, in a first mode, power is not transmitted; in a second mode, power is transmitted in one direction and is not transmitted in a reverse direction thereof; and, in a third mode, power is transmitted in the reverse direction and is not transmitted in the one direction, selects one of the above modes and changes over from one mode to the selected mode.

According the present invention, there may be provided a master-slave manipulator system and an operation input device which are capable of presenting an obstacle and a limit to an operation range as a force feed-back with no use of a motor in the operation input device, and which have high reliability, a small-size and good operability.

Other objects, features and advantages of the invention will become apparent from the following description of the embodiments of the invention taken in conjunction with the accompanying drawings.

DETAILED DESCRIPTION OF THE INVENTION

Explanation will be hereinbelow made of an embodiment according to the present invention with reference to FIGS. 1 to 7.

Figure 1:
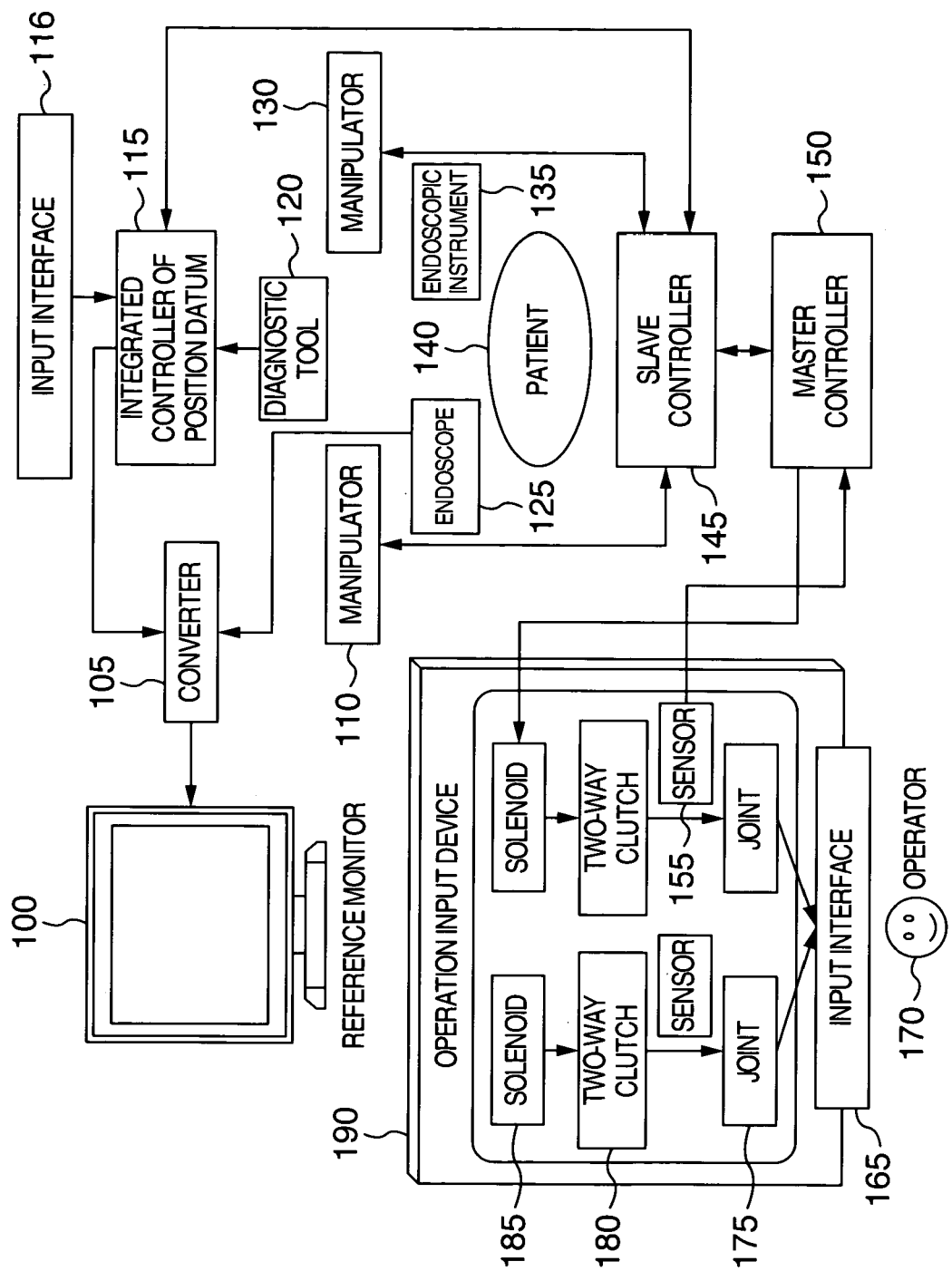
FIG. 1 is a conceptive view illustrating an overall structure of a master-slave manipulation system according to an embodiment of the present invention.

FIG. 1 shows an overall configuration of a master-slave manipulator system according to an embodiment of the present invention, which is used as a surgical support system as an example.

An operator 170 may manipulate an endoscopic instrument 135 which is located at the distal end of a second manipulator 130 with the use of an input interface 165 of an operation input device 190, while referring to the endoscopic instrument 135 an image of which is picked up by an endoscope 125 held by a first manipulator 110. An image displayed on a reference monitor 100 is picked up from an affected part of the patient 140 by the endoscope 125 held by the first manipulator 110, and accordingly, the endoscopic instrument 135 may also fall in the viewing field of the endoscope 125 together with the affected part of the patient 140. It is noted that the first manipulator 110 may be also moved with the use of the operation input device 190, similar to the second manipulator 130.

Data as to the affected part of the patient 140 is acquired by a diagnostic tool 120 before or during surgical operation, and is delivered to an integrated controller of position datum 115. With respect to the date of the affected part acquired by the integrated controller of position datum 115, a safety area where the manipulators 110, 130 may be operated, and a hazard area where the manipulators 110, 130 have to not move are inputted by the interface 116 or an interface 165 of the operation input device 106. The data as to the safety area (a possible operation area) or the hazard range may be displayed on the reference monitor 100 through the intermediary of a converter 105, being overlapped with the image of the endoscope 125.

Data of the manipulators 110, 130 is delivered to a slave controller 145 while data as to positions and orientations of the manipulators 110, 130 is delivered to the integrated controller of position of datum 115. The integrated controller of position of datum 115 compares data as to the set safety area and the set hazard area with data as to the present positions of the manipulators 110, 130, and calculates a direction in which the manipulators 110, 130 should not be moved when the manipulators 110, 130 are to be out of the safety area or to enter the hazard area, and transmits the thus obtained data to the slave controller 140, which in turn transmits the data to a master controller 150.

The master controller 150 energizes solenoids 185 in one or more joints 175 in the operation input device 190 corresponding to the direction in which the manipulators 110, 130 should not be moved, so as to connect power transmission of a two-way clutch 180 in order to restrain the input interface 165 of the operation input device 190 from moving in the direction in which the manipulators 110, 130 should not be moved.

During a normal operation input, the two-way clutch 180 attached to each of the joints 175 is set in a disconnecting condition of power transmission by the solenoid 185, and accordingly, the operator 170 can optionally move the input interface 165. Each joint 175 is provided thereto with sensors 155 which include an encoder and a potentiometer and from which acquired data of displacement of the joint is delivered to the master controller 150. The master controller 150 calculates a direction in which the operator desires to move the manipulators 110, 130 and orientations thereof from the data of displacement of the joint, and transmits the thus calculated data to the slave controller 145. The slave controller 145 therefore calculates inverse kinematics of the manipulators 110, 130 so as to drive the joints of the manipulators 110, 130 in order to cause the manipulators 110, 130 to carry out a motion intended by the operator 170. Thus, the endoscope 125 and the endoscopic instrument are operated as the operator intends.

It is noted that the diagnostic tool 120 may be any one of an MRI unit, a CT unit, an ultrasonic probe, a laser range finder or an endoscope, which can display data of and around an affected part by images, CG or the like. The input interface 116 is a position/orientation input device composed of a mouse, a joystick, a keyboard and the like.

Further, the diagnostic image coordination system of the diagnostic tool 120 and the coordination system of the manipulators 110, 130 can be synthesized by physically constraining the bases of the diagnostic tool 120 and the manipulators 110, 130, or by synthesizing transformation matrix obtained by measuring the diagnostic tool 120 and the manipulators 110, 130 with the use of a three-dimensional position measuring unit which is not shown.

Figure 2:
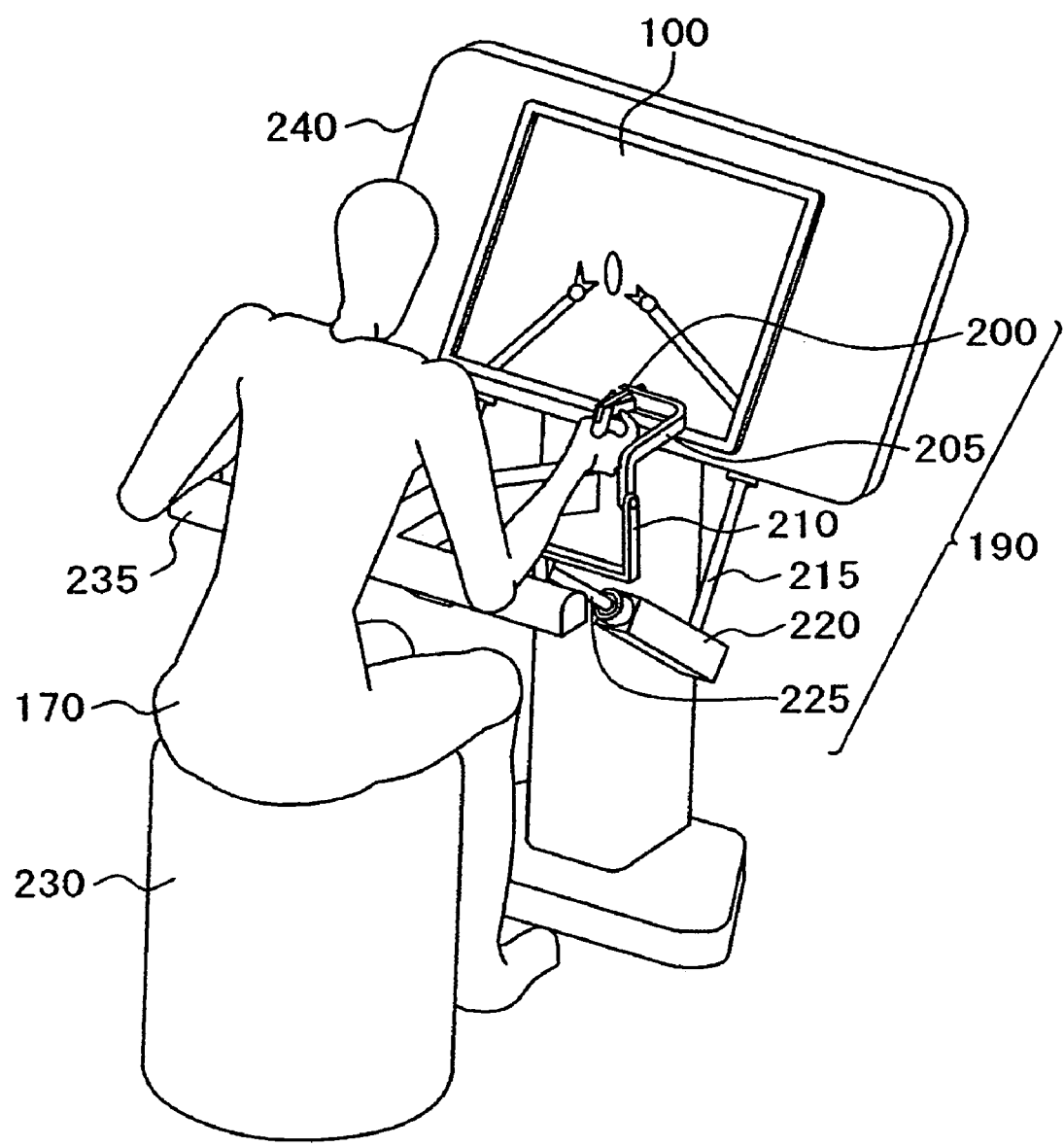
FIG. 2 is a conceptive view illustrating an operation input device shown in FIG. 1.

FIG. 2 shows such a condition that the operator 170 carries out the handling of the manipulators 110, 130 by means of the operation input device 190.

The operator 170 sits on a chair 230, sets his elbows or forearms on the armrest 235 thereof, grips gripping portions 200 serving as the input interface 165 so as to manipulate the gripping portions 200 while he observes the reference monitor 100 in order to move the manipulators displayed on the reference monitor 100 or the viewing field of the endoscope 125 for transmitting an image to the display monitor 100.

The gripping portions 200 are linked to a console 240 through the intermediary of a plurality of links 205, 210, 225, 220, 215 and the like. These links are associated with one another serving as rotating joints and translation joints. By applying the configuration in this embodiment to each joint, as will be explained later, the gripping portions 200 can be optionally moved or can be restrained from moving in a certain direction. The joint mechanism will be detailed later with reference to FIG. 5. In FIG. 2, although the gripping portion 200 is shown only for the right hand of the operator 170, there may be provided another gripping portion 200 serving as a similar interface 165 for the left hand.

It is noted that the arm rest 235 is arranged on members extended from a center pole of the console 240, at a position where it does not physically interfere with the operation range of the operation input devise 190. The member linking the center pole of the console 240 and the armrest 235 is mounted thereon with command input switches for the operation input device 190 and data information presenting lamps which are not shown.

Figure 3:
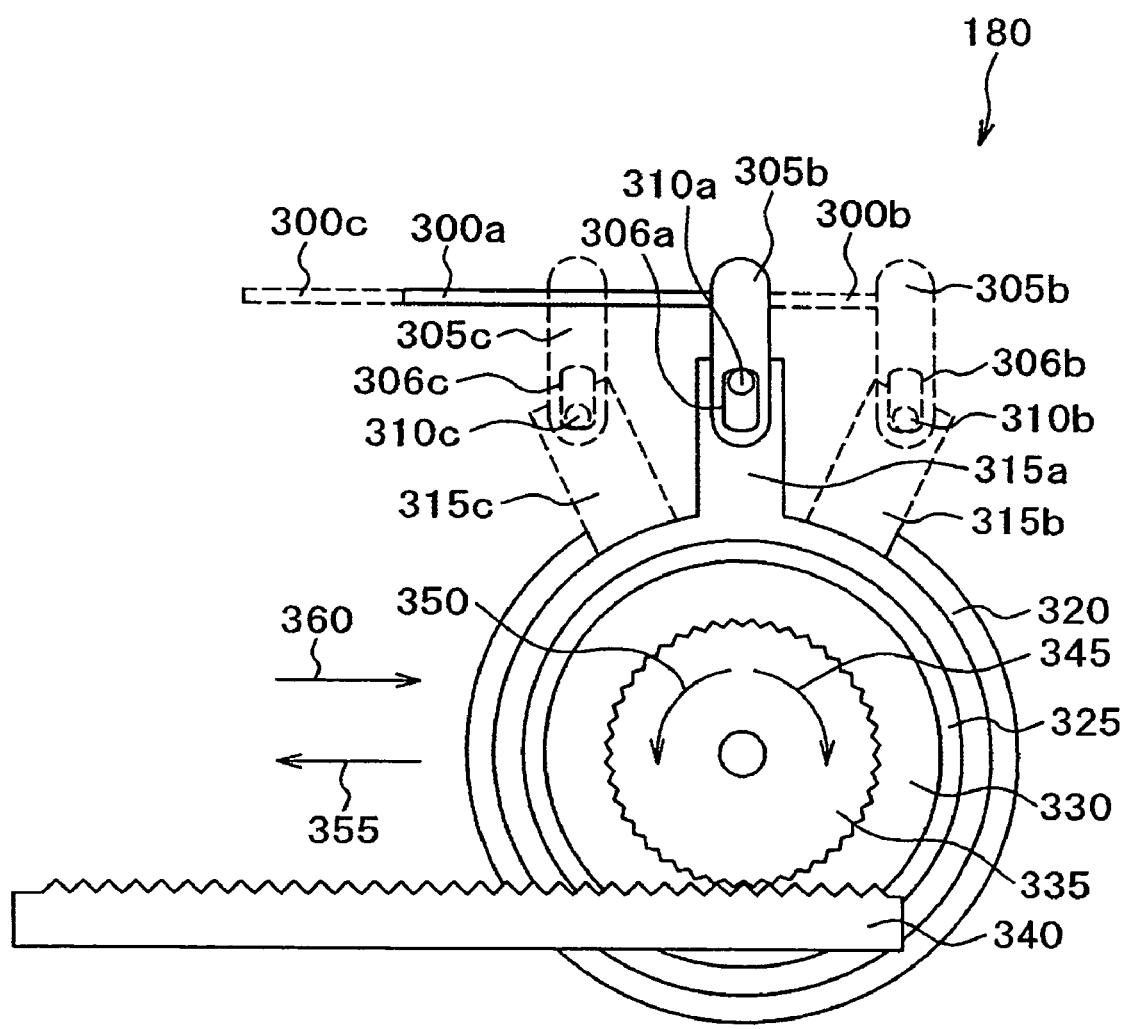
FIG. 3 is a conceptive view illustrating a mode change-over mechanism shown in FIG. 1.

FIG. 3 shows a condition of disconnection and connection of power transmission with the use of the two-way clutch 180 provided in each of the translation joints 175 of the operation input device 190 shown in FIG. 1. In FIG. 3, a condition in which the power transmission of the two-way clutch 180 is disconnected is indicated by the solid line, while a condition in which the power transmission of the two-way clutch 180 is connected in either one of directions thereof but the power transmission is disconnected in the other direction so that the joint may be freely rotated, is indicated by the chain line. It is noted that the components indicated by the solid line are denoted by reference numerals with a suffix a while the components indicated by the chain line are denoted by reference numerals with a suffix b or c. However, when the components will be generally explained, the suffixes a to c will be omitted in the explanation.

Explanation will be briefly made of the features of the two-way clutch 180 with reference to FIG. 3. The two-way clutch 180 is provided with a lever 215, a housing 320 and a bearing 325. When the lever 315 is set in the condition indicated by the solid line 315a with respect to the housing 320, a shaft 330 arranged on the inner diameter side of the bearing 325 can be freely rotated. When the lever 315 is turned to the right side in the figure so that the lever 315 is set on the right side with respect to the housing 320 as indicated by the chain line 315b, the shaft 330 arranged on the inner diameter side of the bearing 325 can not be rotated in the direction of the arrow 345 but may be freely rotated in the direction of the arrow 350. When the lever 315 is turned to the left side in the figure so that the lever 315 is set on the left side with respect to the housing 320 as indicated by the chain line 315c, the shaft 330 arranged on the inner diameter side of the bearing 325 can not be rotated in the direction of the arrow 350 but may be freely rotated in the direction of the arrow 345.

The link 305 integrally incorporated with the rod 300 has an elongated hole 306, and is connected to the lever 315 through the intermediary of the shaft 310, which is integrally incorporated with the lever 315. When the lever 310 is located in the condition of the lever 315c indicated by the solid line with respect to the housing 320, the shaft 330 arranged on the inner diameter side of the bearing 325, can be freely rotated. The shaft 330 is operated in synchronization with a pinion gear 335 coaxial therewith. Further, the pinion gear 335 is meshed with a rack 340, which is stationary. Since the pinion gear 335 is meshed with the stationary rack 340 and is therefore constrained, the housing 320 may be freely moved in a direction 355 or 360 when a force is exerted to the housing 320 in the direction 355 or 360 if the lever 315 is set in the condition of the lever 315a indicated by the solid line.

When a force from the left side is applied to the rod 300a indicated by the solid line by means of the solenoid 185 or the like so as to set the condition of the rod 300b indicated by the chain line, the link 305 integrally incorporated with the rod 300b is turned into the condition of the link 305b indicated by the chain line. At this stage, the shaft 310 is moved through the elongated hole 306 in the link 305 so as to fall in the condition of the shaft 310b indicated by the chain line, and accordingly the lever 315 integrally incorporated with the shaft 310 is changed into the condition of the lever 315b indicated by the chain line. At this stage, according to the function of the two-way clutch 180, the shaft 330 and the pinion gear 335 moved integrally therewith can not be rotated in the direction of the arrow 345 but may be moved only in the direction of the arrow 350. Thus, even though any force is exerted to the housing 320 in the direction of the arrow 360, the housing 320 can not be moved in the direction of the arrow 360. Meanwhile, it may be freely moved in the direction of the arrow 355.

On the contrary, when the rod 300a is turned into the rod 300c indicated by the chain line by applying a force from a right side thereto by means of the solenoid 185 (refer to FIG. 1 and FIG. 4) or the like, the link 305 integrally incorporated with the rod 300c is turned into a condition of the link 305c indicated by the chain line. The shaft 310 is moved through the elongated-hole 306 in the link 305 and is turned into a condition of the shaft 310c indicated by the chain line, and the lever 315 integrally incorporated with the shaft 310 is turned into a condition of the lever 315c indicated by the chin line. At this time, according to the function of the two-way clutch, the shaft 330 and the pinion gear 335 moved integrally therewith can not be rotated in the direction of the arrow 350, but may be rotated only in the direction of the arrow 345. Thus, the housing 320 can not be moved in the direction of the arrow 355 even though a force is exerted to the housing 320 in the direction of the arrow 355. Meanwhile, it may be freely moved in the direction of the arrow 360.

Figure 4:
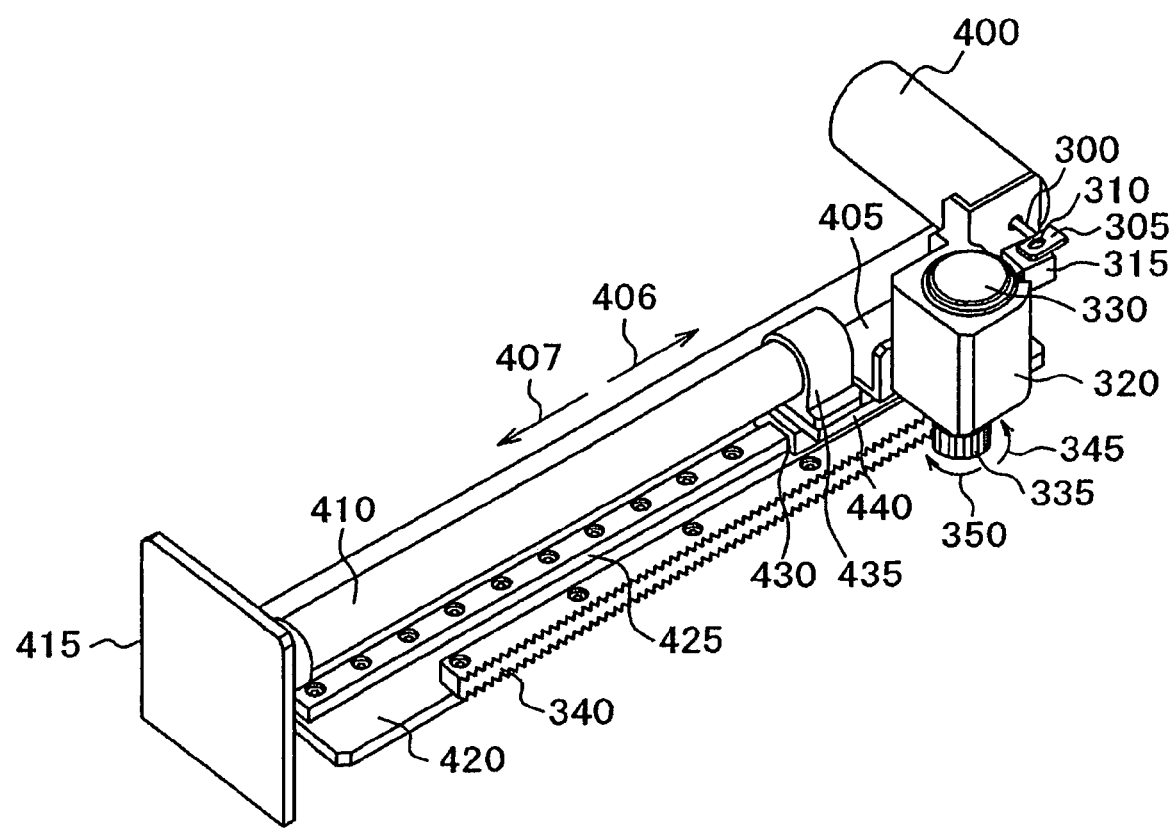
FIG. 4 is a perspective view illustrating the mode change-over mechanism shown in FIG. 1, which is used in a translation joint.

FIG. 4 is a perspective view illustrating the translation joint mechanism for one axial part using the two-way clutch 180 shown in FIG. 3. The translation join mechanism moves a rod 410 in the direction of the arrow 406 or the direction of the arrow 407 with respect to a base 420, and some similar joint mechanisms are connected subsequent to the base 415 of the next joint, and are finally linked to the gripping portions 200 (refer to FIG. 2).

The base 420 is fixed thereto with a linear guide rail 425 and a rack 340, and a guide base 440 is attached to a guide 430 moved on the linear guide rail 425. On the guide base 440, a rod 410 is secured by means of a rod fixture 435, and the housing 320 is secured by a clutch fixture 405. To the housing 320 are fixed the two-way clutch and a 3 position solenoid 400 (corresponding to the solenoid 185 shown in FIG. 1) for moving a lever of the two-way clutch. The 3 position solenoid 400 may move and hold the rod 300 in three conditions (rod 300a, 300b and 300c) as explained with reference to FIG. 3.

When an input force exerted by the operator 170 is transmitted to the base 415 of the next joint through the intermediary of the gripping portions 200 (refer to FIG. 2), a force along the direction of the arrow 406 or 407 is applied to this joint. If the 3 position solenoid 400 holds the rod 300 in the condition of the rod 300a indicated by the solid line, the power transmission of the two-way clutch is disconnected and accordingly, the shaft 330 and the pinion gear 335 may be freely rotated. Thus, the pinion gear 335 may be moved on the rack 340 while it is freely rotated, and accordingly, the guide 430 may be freely moved on the linear guide rail 425 in the direction of the arrow 106 or 107 in response to a force exerted to the base 415 of the next joint.

Meanwhile, it is estimated that an input force applied by the operator is transmitted to the base 415 of the next joint through the intermediary of the gripping portions 200 (refer to FIG. 2), and accordingly, a force in the direction of the arrow 406 is exerted to this joint. Further, it is estimated that at this time, the master controller 150 (refer to FIG. 1) calculates such a condition that if the operation input device 190 is moved in the direction of the arrow 406, there is presented a hazard area in the moving direction of the manipulator 110 or 130 which is moved in association with the operation input device 190, and thus, the manipulator 110 or 130 should not be moved in the direction. In this case, the master controller 150 issues a signal for energizing the 3 position solenoid 400 so as to move the lever 315 and to connect the power transmission function of the two-way clutch, resulting in such a condition that the pinion gear 335 can not be rotated in the direction of the arrow 345 but may be rotated in the direction of the arrow 350. Accordingly, the guide 430 may move in the direction of the arrow 407 but can not move in the direction of the arrow 406 according to the meshing between the pinion gear 335 and the rack 340. Thus, the operator 170 may input his manipulation in the direction of the arrow 407 on the safety side but can not input his manipulation in the direction of the arrow 406 toward the hazard area, thereby it is possible to solve such a problem that the manipulator 110 or 130 is moved into the hazard range.

Similarly, it is estimated that a force in the direction of the arrow 407 is exerted to the base 415 of the next joint, and the master controller 150 (refer to FIG. 1) calculates such a condition that at the time if the operation input device 190 is to be moved in the direction of the arrow 407, there is presented a hazard area in the moving direction of the manipulator 110 or 130 which is moved in association with the operation input device 190, and accordingly, the manipulator should not be moved in this direction. In this case, similarly to the above case, the master controller 150 issues a signal for energizing the 3 position solenoid 400 so as to move the lever 315 and to connect the power transmission connection of the two-way clutch, resulting in such a condition that the pinion gear 335 can not be rotated in the direction of the arrow 350 but may be rotated in the direction of the arrow 345. Thus, the guide 430 may move in the direction of the arrow 406 but can not move in the direction of the arrow 407 according to the meshing between the pinion gear 335 and the rack 340.

It is noted that the displacement amount of the joint is measured by a linear encoder which is although not shown, and accordingly, a manipulation input amount may be acquired by the master controller 150.

Figure 5:
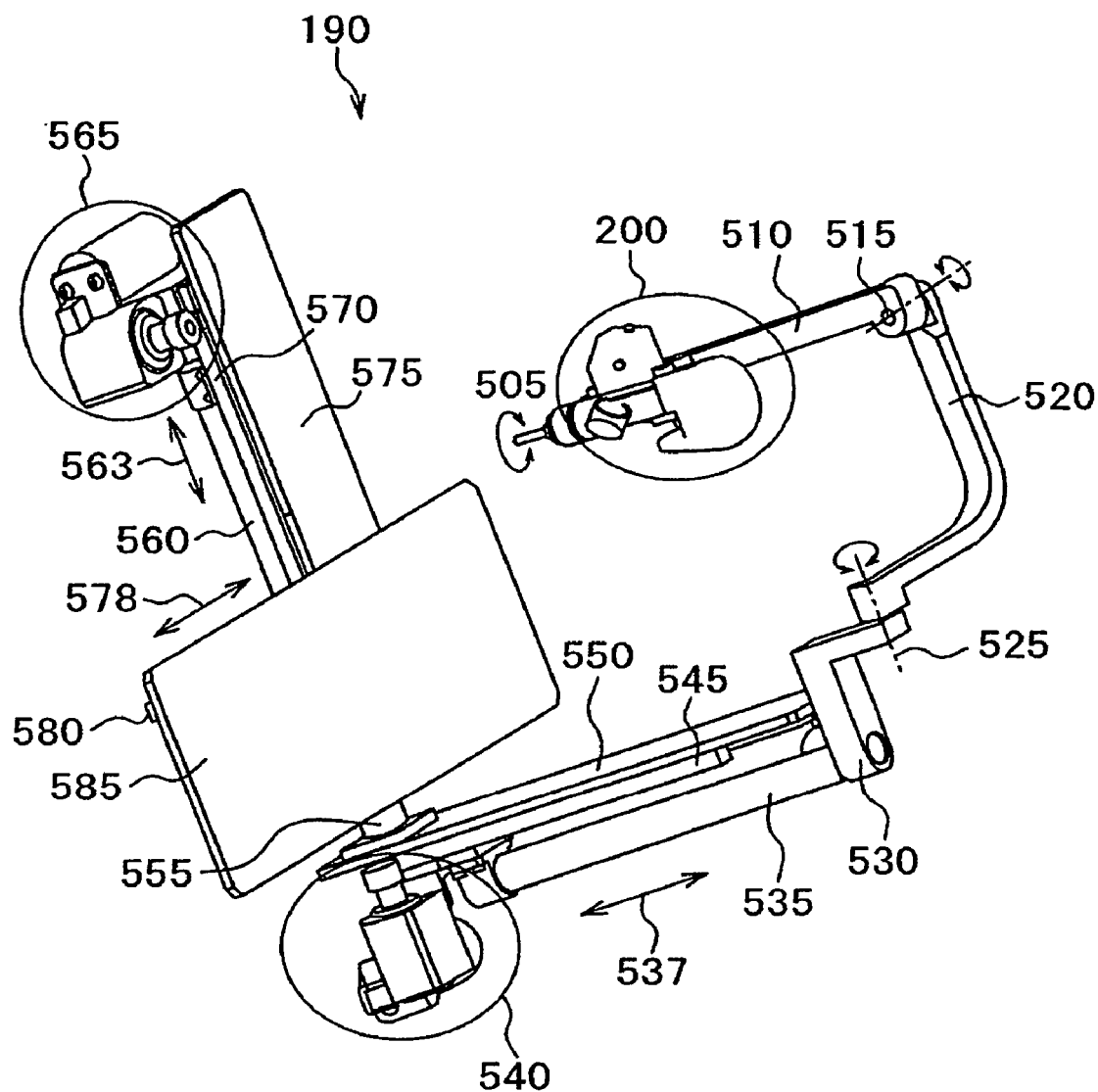
FIG. 5 is a perspective view illustrating an operation input device utilizing the mode change-over mechanism shown in FIG. 4.

FIG. 5 shows an entire configuration of the operation input device 190 in this embodiment from which the console 240 is eliminated.

A base 585 is attached to the rear surface of the console 240 shown in FIG. 2. A base 575 and a linear guide rail 580 fixed to the rear surface of the base 585 are linked to each other through the intermediary of translation joints so that the base 575 is moved on the linear guide rail 580 in the direction of the arrow 578, that is, in the left and right directions. A mode change-over mechanism which according to the present invention is also attached to this translation joints which are moved in the direction of the arrow 578 although it is hidden behind the base 585 so that it is invisible.

A rod 560 is translated in the direction of the arrow 563 which is a vertical direction with respect to the base 575 through the intermediary of a mode change-over mechanism 565 meshed with a rack 570 attached to the base 575.

A rod 535 is translated with respect to a base 550 in the direction of the arrow 537 which is a longitudinal direction through the intermediary of a mode change-over mechanism 540 meshed with a rack 545 fixed to the base 550.

A fixture 530 mounted to the rod 535 is connected to a link 520 through the intermediary of a shaft 525, and the link 520 serves as a rotating joint by means of the shaft 525. The link 520 is connected a link 510, using the shaft 515 as a rotary shaft, and the link 510 is connected to the gripping portions 200 through the intermediary of the shaft 505.

The operation input device 190 shown in FIG. 5 is composed of three translation joints and three rotating joints, and accordingly, the operator may input positions and orientations in six degrees of freedom. It is noted that the gripping portions 200 are provided with opening and closing joints for the endoscopic equipment.

The translation joints corresponding to the arrows 563, 537 are provided with constant force springs which are not shown, in order to compensate the dead weight of the operation input device. Thus, the operator 170 may freely manipulate the operation input device 190 with no feel of the dead weight thereof when the manipulation is made by holding the gripping portions 200.

Although there are not shown in FIG. 5 the mode change-over mechanisms on the shafts 525, 515, 505 serving as rotating joints, the mode change-over mechanism may be materialized in such a way that the shaft 330 shown in FIG. 3 is used as a joint shaft while the housing 220 is fixed to a link of the base, and a link of the next joint is secured to the shaft 330, instead of the pinion gear 350.

As shown in FIG. 5, by using the mode change-over mechanisms in only three translation joints, the input of an orientation is optional, and accordingly, only the input of a position may be limited. By also providing the mode change-over mechanism in the three rotating joints, the position and orientation in six degrees of freedom may be limited.

Figure 6:
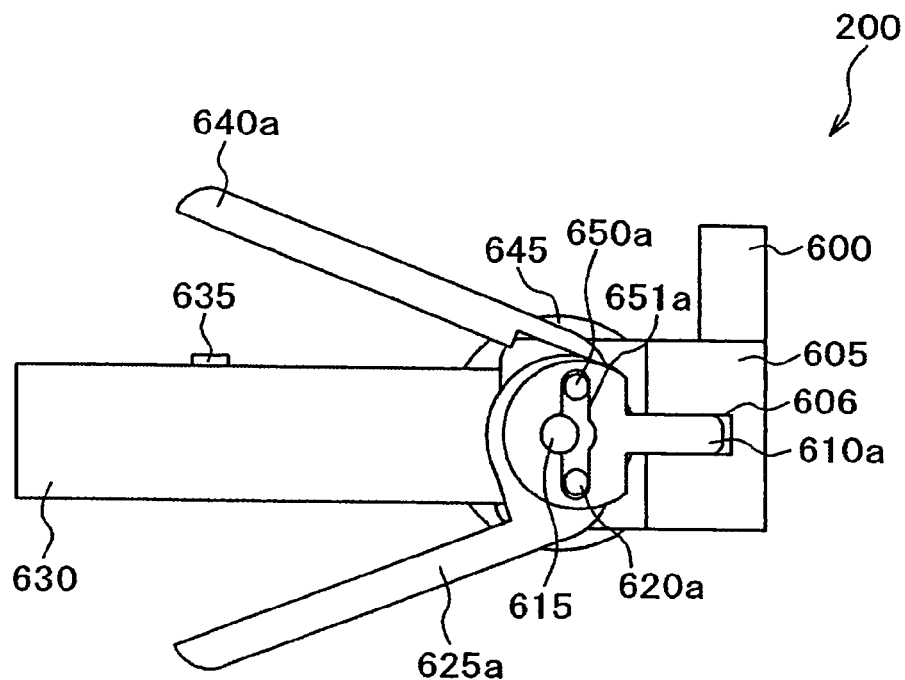
FIG. 6 is a conceptive view illustrating a grip input device shown in FIG. 5, in an opened condition.
Figure 7:
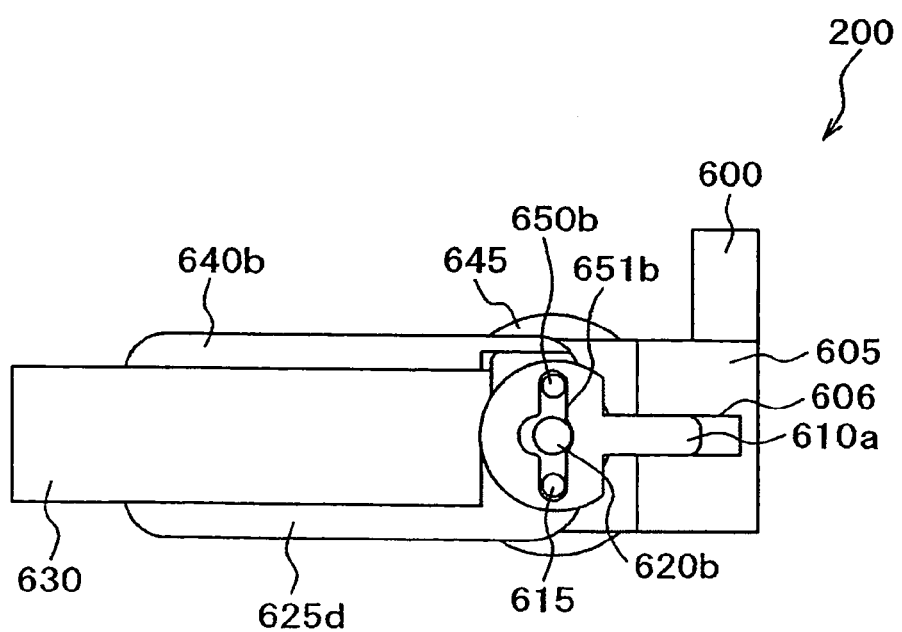
FIG. 7 is a conceptive view illustrating the grip input device shown in FIG. 5, in a closed condition.

FIGS. 6 and 7 are plan views illustrating the gripping portion 200 in this embodiment in different conditions. Movable components in the gripping portion 200 are denoted by reference numerals with a suffix a in the condition shown in FIG. 6, and with a suffix b in the condition shown in FIG. 7. However, the components will be explained being generally denoted by reference numerals with no suffixes a to b.

In this gripping portion 200, the forefinger and the thumb touch blades 625, 640 so as to input an opening and closing manipulation to the endoscopic instrument 165. As to the features of the gripping portion 200, even by moving only the blade 640 with respect to a base 630, the blade 625 may be also symmetrically moved, and on the contrary, only by moving the blade 625, the blade 640 may be also similarly moved. Thus, for the opening and closing manipulation, it is possible to accept three cases, that is, a person desires to use only his thumb, or a person desires only his forefinger, and a person desires to use both thumb and forefinger.

A cam retainer 605 integrally incorporated with the base 630 is formed therein with a hole 606 through which a cam plate 610 may be translated. A shaft 615 is serving as a rotating center shaft of the blades 625, 640, and pierces through the base 630 so as to serve as a mode change-over mechanism 645. Since the shaft 615 is rotated integrally with the blade 625, the opening angle of the blades may be limited by the mode change-over mechanism 645. The mode change-over mechanism 645 includes a 3 position solenoid 600. Further, the opening angle of the blades may be acquired by an encoder which is not shown.

Further, the shaft 615 pierces through a cam hole 651 in the cam plate 610, and a shaft 650 integrally incorporated with the blade 640 and a shaft 620 integrally incorporated with the blade 625 pierce through the cam hole 651 in the cam plate 610.

When a force is exerted to the blade 640a shown in FIG. 6 in the closing direction similar to the blade 640b shown in FIG. 7, the blade 640a is rotated about the shaft 615 as a center, and the shaft 650a moved integrally with the blade 640a is also moved around the shaft 615 as a rotating center. The shaft 650a moves the cam plate 610a shown in FIG. 6, through the cam hole 651a, as is similar to the cam plate 610b shown in FIG. 7. By moving the cam plate 610, similar to the cam plate 610b shown in FIG. 7, a force is exerted to the shaft 620a so that the shaft 620a is turned into the shaft 620b shown in FIG. 7 through the cam hole 651a. Thus, the blade 625a integrally incorporated with the shaft 620a is turned into the blade 625b.

In this embodiment, according to the provision of a mechanism for simultaneously opening two blades, it may be manufactured in a simple and inexpensive way in comparison with a parallel link mechanism which has been conventionally used in general.

Further, with the use of the mode change-over mechanism 645, the opening degree of the gripping portion may be limited or the gripping portion may be held in a closed condition. In the operation in which the affected part is to be pressed and opened with the use of the endoscopic instrument blades 640, 625, if it is desired to limit the opening degree of the endoscipic equipment 135, since the opening degree of the endoscopic equipment blades 640, 625 may be limited, it is possible to enhance the safety. Further, since the closed condition may be maintained, the operator 170 may eliminate the necessity of gripping with a strong force while he grips an object such as a needle, thereby it is possible to alleviate fatigue or the like. It is noted that the blades 640, 625 are normally opened by springs which are not shown, as shown in FIG. 6.

An opening and closing base 630 is provided thereto with a micro-switch 635 which responds when it is firmly pressed after the blade 640a is turned into the blade 640b. In this embodiment, when the micro-switch 635 responds, the mode change-over mechanism 645 is operated so that the blades 640, 625 are held in the closed condition. It is noted that another button which is not shown is depressed by a finger, and accordingly, the blades 640, 625 may be released from the closed condition.

When the opening degree of the endoscopic equipment is to be limited, a maximum opening degree has been previously inputted through the input interface 116, and then, the mode change-over mechanism 645 is used.

Further, in the mode change-over mechanism 645, the directions of connection of the power transmission and the disconnection thereof are controlled by the master controller 150, and accordingly, softness and hardness upon contact of the manipulator arm with an object may be exhibited as a force feed-back in addition to the exhibition of an obstacle or a wall of a hazard area. That is, the controller 150 selects the mode of the mode change-over mechanism multiple times and in a variable manner of the duty ratio so as to finely change over the connection, and accordingly, a force feed-back is exhibited when the arm of the manipulator 110 or 130 touches the object.

As stated above, in this embodiment, when no presentation of a safety area or a hazard area is required, the operation input device 190 may be optionally moved, but when the presentation of the safety area or the hazard area is required, the motion toward the hazard area can be limited with no use of a motor while the motion toward the safety area may be optionally made. Further, an operating range limited by the operator and an obstacle can be presented as a force feed-back without using a motor in the operation input device 190, and accordingly it is extremely effective in view of miniaturization and control stability of the operation input device 19, which may exhibits enhanced operability thereof. Further, since no motor is used therein, it is highly effective in an environment in which the affection by noises is desired to be reduced, such as an MRI environment. Further since no motor is used, the operation input device may be manufactured at a low cost.

Further, even with the opening manipulation of the endoscopoic equipment 135, the opening degree of the endoscopic equipment 135 may be limited during press-opening operation by the endoscopic equipment 135, and a fatigue which is caused by pressing the gripping portions when the endoscopic equipment 135 is closed may be alleviated, thereby it is possible to enhance the operability.

It is noted that although explanation has been made of the embodiment in which the two-way clutch is used as the power transmission disconnection and connection mechanism which materializes the mode change-over mechanism, two one-way clutches and two solenoids may be also used to materialize the mode change-over mechanism.

Although explanation have been made of the operation input device in the surgical support manipulator in this embodiment, the present invention may be also implemented as an operation input device such as a humanoid arm or an arm of an industrial manipulator.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A master-slave manipulator system comprising:
a manipulator having an arm;

an operation input device for moving said arm of said manipulator; and a controller for controlling said manipulator and said operation input device, wherein said operation input device comprises on joints a motion-direction limitation changeover mechanism having modes: of which, in one mode, the motion on the joint is limited;

in the other mode the motion of one direction on the joint is free, selecting one of the above modes and changing over from one mode to the selected mode.

2. A master-slave manipulator system as set forth in claim 1, wherein there are provided a sensor or a diagnostic tool capable of acquiring geometrical data and data of the obstacle in an operation range of said arm of said manipulator and a means for setting an area where said arm of said manipulator may be operated in accordance with the geometrical data and the data of the obstacle detected by said sensor or said diagnostic tool in the operation range of said arm of said manipulator, and said controller restrains said operation input device from being operated in an area where said arm of said manipulator should not be moved, with the use of said motion-direction limitation changeover mechanism which is arranged on each of the joints in said operation input device, when said arm of said manipulator is to be manipulated in the area where said arm of said manipulator should not be moved.

3. A master-slave manipulator system as set forth in claim 1, wherein said operation input device comprises a grip opening and closing mechanism capable of having functions of said motion-direction limitation changeover mechanism, and capable of optionally limiting a degree of opening of a grip.

4. A master-slave manipulator system as set forth in claim 2, wherein Magnetic Resonance Imaging (MRI) unit is used as the diagnostic tool for acquiring the geometrical data in the operation range of said arm of said manipulator.

5. A master-slave manipulator as set forth in claim 2, wherein a Computed Tomography (CT) unit is used as the diagnostic tool for acquiring the geometrical data in the operation range of said arm of said manipulator.

6. A master-slave manipulator system as set forth in claim 1, wherein said controller controls the selection of said changeover mechanism so as to limit the operation range of said arm of said manipulator.

7. A master-slave manipulator system as set forth in claim 1, wherein said controller selects the mode of said motion-direction limitation changeover mechanism multiple times and in a variable manner of duty ratio so as to finely change over the connection, thereby, presenting a force feed-back when said arm of said manipulator makes contact with an object.

8. An operation input device for moving an arm of a manipulator in a master-slave manipulator system, wherein a mode changeover mechanism having three modes: of which, in a first mode, power is not transmitted; in a second mode, power is transmitted in one direction and is not transmitted in a reverse direction thereof; and, in a third mode, power is transmitted in the reverse direction and is not transmitted in the one direction, selecting one of the above modes and changing over from one mode to the selected mode is provided on joints.

9. A master-slave manipulator system comprising:

a manipulator having an arm;

an operation input device for moving said arm of said manipulator; and a controller for controlling said manipulator and said operation input device, wherein said operation input device comprises on joints a motion-direction limitation changeover mechanism having modes: of which, in one mode, the motion on the joint is free;

in the other mode, the motion of one direction on the joint is limited, selecting one of the above modes and changing over from one mode to the selected mode, wherein said motion-direction limitation changeover mechanism which is arranged on each of the joints in said operation input device comprises a two-way clutch, a 3 position solenoid, and a translation joint mechanism utilizing a rack and a pinion.

10. A master-slave manipulator system comprising:

a manipulator having an arm;

an operation input device for moving said arm of said manipulator; and a controller for controlling said manipulator and said operation input device, wherein said operation input device comprises on joints a motion-direction limitation changeover mechanism having modes: of which, in one mode, the motion on the joint is free;

in the other mode, the motion of one direction on the joint is limited, selecting one of the above modes and changing over from one mode to the selected mode, wherein said motion-direction limitation changeover mechanism which is arranged on each of the joints in said operation input device comprises a two-way clutch, a three position solenoid and a rotating joint mechanism utilizing two links constituting the joint.

* * * * *